United States Patent
Qiu et al.

(10) Patent No.: US 8,062,664 B2
(45) Date of Patent: Nov. 22, 2011

(54) PROCESS FOR PREPARING FORMULATIONS OF LIPID-REGULATING DRUGS

(75) Inventors: Yihong Qiu, Vernon Hills, IL (US); Jacqueline Wardrop, Wilmette, IL (US)

(73) Assignee: Abbott Laboratories, Abbott Park, IL (US)

( * ) Notice: Subject to any disclaimer, the term of this patent is extended or adjusted under 35 U.S.C. 154(b) by 1590 days.

(21) Appl. No.: 10/883,933

(22) Filed: Jul. 2, 2004

(65) Prior Publication Data

US 2005/0112192 A1  May 26, 2005

Related U.S. Application Data

(60) Provisional application No. 60/484,271, filed on Nov. 12, 2003.

(51) Int. Cl.
*A61K 9/48* (2006.01)
(52) U.S. Cl. .............................. 424/464; 264/109
(58) Field of Classification Search .................. None
See application file for complete search history.

(56) References Cited

U.S. PATENT DOCUMENTS

| | | | |
|---|---|---|---|
| 4,058,552 A | 11/1977 | Mieville | |
| 4,739,101 A * | 4/1988 | Bourgogne et al. | 560/61 |
| 4,800,079 A | 1/1989 | Boyer | |
| 4,895,726 A | 1/1990 | Curter et al. | |
| 4,961,890 A | 10/1990 | Boyer | |
| 5,460,828 A * | 10/1995 | Santus et al. | 424/489 |
| 5,645,856 A | 7/1997 | Lacy et al. | |
| 6,372,790 B1 * | 4/2002 | Bonhomme et al. | 514/555 |
| 6,383,517 B1 | 5/2002 | Qiu et al. | |
| 2004/0137055 A1 | 7/2004 | Criere et al. | |

FOREIGN PATENT DOCUMENTS

| | | |
|---|---|---|
| CA | 2253769 | * 11/1998 |
| EP | 0793958 | 2/1997 |
| EP | 0 625 351 | 7/1999 |
| JP | 4-103525 A | 4/1992 |
| JP | 2002-507569 | 3/2002 |
| JP | 2003-504331 | 9/2003 |
| WO | 82/01649 | 5/1982 |
| WO | 99/48499 | 9/1999 |

OTHER PUBLICATIONS

"Remington: The Science and Practice of Pharmacy," 19th Edition, A.R. Genaro Editor, Mack Publishing (1995).*
Palmieri, G. F. et al., "Characterization and dissolution studies of PEG 4000/fenofibrate solid dispersions," S.T.P. Pharma Sciences 6(3):188-194 (1996).

* cited by examiner

*Primary Examiner* — Shanon A Foley
(74) *Attorney, Agent, or Firm* — Lisa V. Mueller; Michael Best & Friedrich LLP

(57) ABSTRACT

A process for preparing a formulation of a lipid-regulating drug is disclosed, the process comprising dissolving lipid-regulating drug in a solvent free of surfactant to form a solution, premixing an excipient to form an admixture, wet granulating the solution and admixture to form a granulated admixture, drying the granulated admixture and utilizing the dried material to obtain a final dosage form.

16 Claims, 1 Drawing Sheet

DISSOLUTION PROFILES OF FENOFIBRATE CAPSULES, 67 mg, MANUFACTURED VIA SOLVENT GRANULATION COMPARED TO MARKETED PRODUCT

PROCESS FOR PREPARING FORMULATIONS OF LIPID-REGULATING DRUGS

This application claims priority from U.S. Provisional Patent Application Ser. No. 60/484,271, filed Nov. 12, 2003.

FIELD OF THE INVENTION

The present invention relates to a new process for preparing solid formulations of lipid-regulating drugs.

BACKGROUND OF THE INVENTION

2-[4-(4-chlorobenzoyl)phenoxy]-2-methyl-propanoic acid, 1-methylethylester, also known as fenofibrate, is representative of a broad class of compounds having pharmaceutical utility as lipid-regulating drugs. More specifically, this compound is part of a lipid-regulating drug class of compounds commonly known as fibrates, and is disclosed in U.S. Pat. No. 4,058,552.

Fenofibrate has been prepared in several different formulations, c.f., U.S. Pat. Nos. 4,800,079 and 4,895,726. 4,895,726 discloses a co-micronized formulation of fenofibrate and a solid surfactant.

U.S. Pat. No. 4,961,890 discloses a process for preparing a controlled release formulation containing fenofibrate in an intermediate layer in the form of crystalline microparticles included within pores of an inert matrix. The formulation is prepared by a process involving the sequential steps of dampening said inert core with a solution based on said binder, then projecting said fenofibrate microparticles in a single layer onto said dampened core, and thereafter drying, before said solution based on said binder dissolves said fenofibrate microparticles, and repeating said three steps in sequence until said intermediate layer is formed.

European Patent Application No. EP0793958A2 discloses a process for producing a fenofibrate solid dosage form utilizing fenofibrate, a surface active drug and polyvinyl pyrrohidone in which the fenofibrate particles are mixed with a polyvinyl pyrrolidone solution. The thus obtained mixture is granulated with an aqueous solution of one or more surface active drugs, and the granules thus produced are dried.

PCT Publication No. WO82/01649 discloses a fenofibrate formulation having granules that are comprised of a neutral core that is a mixture of saccharose and starch. The neutral core is covered with a first layer of fenofibrate, admixed with an excipient and with a second micropcrous outer layer of an edible polymer.

U.S. Pat. No. 5,645,856 discloses the use of a carrier for hydrophobic drugs, including fenofibrate, and pharmaceutical compositions based thereon. The carrier comprises a digestible oil and a pharmaceutically-acceptable surfactant component for dispersing the oil in vivo upon administration of the carrier, which comprises a hydrophilic surfactant, said surfactant component being such as not to substantially inhibit the in vivo lipolysis of the digestible oil.

U.S. Pat. No. 6,383,517 discloses a process for preparing a solid formulation of fenofibrate comprising dissolving the fenofibrate in a surfactant solution, premixing an excipient, wet granulating the mixture, drying the mixture and forming a finished dosage form.

The prior art processes obtain small particles of fenofibrate by the use of co-micronization steps and/or require the presence of surfactants. These processes result in formulations that may not have maximized dissolution characteristics, and may cause gastro intestinal irritation.

It is an object of the present invention to provide small particles of lipid regulating drugs, more preferably fenofibrate, having comparable dissolution and absorption characteristics to those particles of such drugs prepared by the prior art techniques without the need of micronizing the lipid-regulating drug or utilizing surfactants.

SUMMARY OF THE INVENTION

The present invention is directed to a process for preparing a solid formulation of a lipid regulating drug.

The process comprises dissolving the lipid-regulating drug in a solvent free of surfactants, premixing one or more excipients to generate an admixture, wet granulating the lipid-regulating drug solution and the premix to form a granulated drug admixture and drying the mixture. The dried granulated admixture may then be sized and formed into a final dosage form.

The mixture may be granulated by techniques well-known in the art, preferably by a fluidized bed or by means of a low shear or high shear mixer.

The final oral dosage form may be prepared by techniques wellknown to those skilled in the art by sizing the mixture and dry blending the resultant particles with excipients into the final oral dosage form, preferably as a tablet or capsule.

The formulation thus produced may be administered directly as a granulated product, diluted into an appropriate vehicle for administration, encapsulated into hard gelatin shells or capsules for administration, or administered by other means obvious to those skilled in the art.

DETAILED DESCRIPTION OF THE INVENTION

Figure 1:
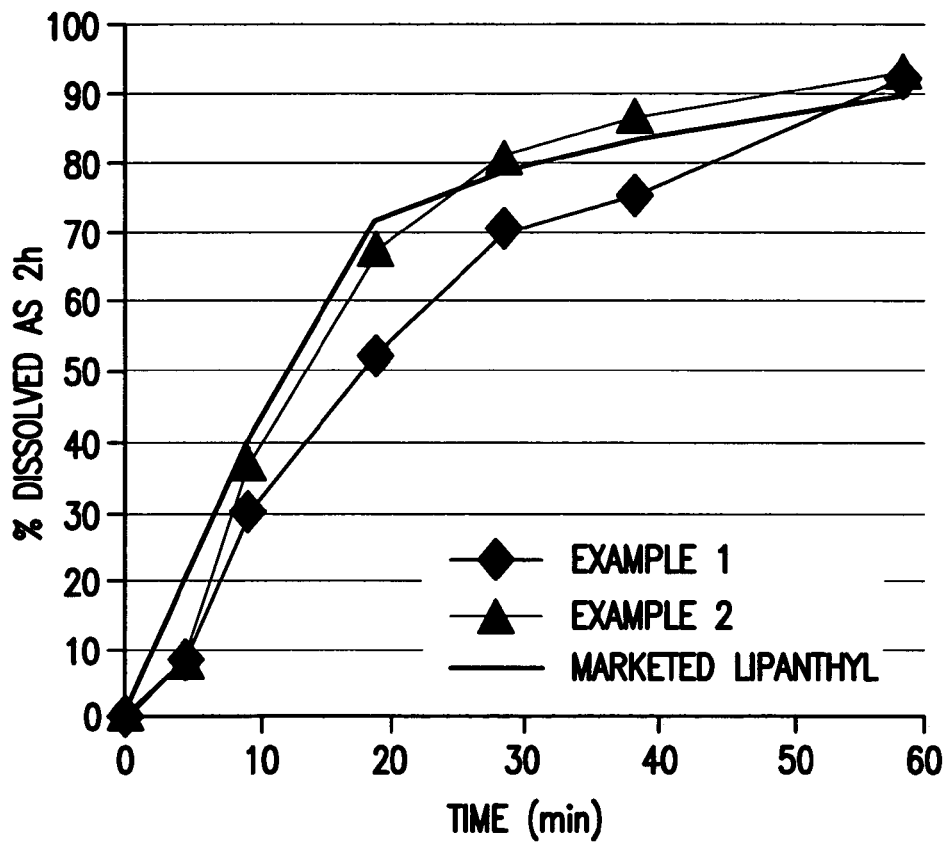
FIG. 1 is a graph showing the dissolution characteristics of representative compositions prepared by the process of the present invention and a prior art composition.

The lipid regulating drug may be any suitable pharmaceutically active compound, preferably a fibrate and more preferably fenofibrate.

The bulk lipid-regulating drug can be prepared by any available method, as for example the compound fenofibrate may be prepared by the procedure disclosed in U.S. Pat. No. 4,658,552, or the procedure disclosed in U.S. Pat. No. 4,739,101, both herein incorporated by reference.

The lipid-regulating drug is then dissolved in a solution with a suitable solvent such as, for example, acetone, methylene chloride, ethanol or chloroform in amounts ranging from 0.5 to 8.0, preferably 1.0 to 5.0 parts by weight lipid lowering drug A premix of excipients is prepared by conventional techniques. Suitable excipients include, for example, binders, fillers and disintegrants such as lactose, starch, polyvinyl pyrrolidone, sodium starch glycolate and microcrystalline cellulose.

The lipid-regulating drug solution and excipient premix are then mixed together. The resulting mixture is then granulated, for example, in a fluidized bed or a low or high shear mixer and dried by well-known solvent evaporation techniques, as for example, spray drying, fluid bed, tray drying, rotary atomizing, spinning disk drying, or evaporation under atmospheric or reduced pressure. The resultant material may then be sized, if necessary and formulated into a finished dosage form, for example, a tablet or capsule by conventional techniques such as direct compression or other means.

The elimination of the surfactant results in a process having reduced raw material and capital costs, ease of manufacture, potential reduction of gastrointestinal side effects and the ability to prepare tablets and capsules more readily. The invention will be understood more clearly from the following non-limiting representative examples:

EXAMPLE 1

Fenofibrate (25 g) was dissolved in 10 mL acetone. Lactose anhydrous (67 g), Povidone K30 (4 g) and sodium starch glycolate (4 g) were premixed. The premix was granulated with the above solution. The wet granules were tray dried overnight in an oven at approximately 40-55° C. The dried granules were sieved through a screen, the 30-120 mesh portion was collected and filled into a hard gelatin capsule.

In vitro dissolution rate of the capsules were compared with that of the reference, Lipanthyl, the marketed capsule product, which contains the same amount of the active. USP apparatus II was used for testing. The test conditions were: paddle speed=50 rpm; dissolution medium=50 mM SDS solution; temperature=37 ° C. Dissolution samples were removed at pre-determined time points and analyzed by UV spectrophotometry at 286 nm.

EXAMPLE 2

Fenofibrate (25 g) was dissolved in 10 mL acetone. Lactose anhydrous (57 g), Aircel pH 101 (10 g), Povidone K30 (4 g) and sodium starch glycolate (4 g) were premixed. The premix was mixed with above solution. The wet mass was tray dried in an oven at 40-55° C.

The dried solid was milled, sieved through a screen and the 30-120 mesh portion collected. The collected particles were filled into a hard gelatin capsule.

EXAMPLE 3

In vitro dissolution rates of the capsules produced in Examples 1 and 2 were compared with that of the reference, Lipanthyl, the marketed capsule product, which contains the same amount of the active. USP apparatus II was used for testing. The test conditions were: paddle speed=50 rpm; dissolution medium=50 mM SDS solution; temperature 37° C. 5 mL dissolution samples were removed at pre-determined time points and assayed by UV spectrophotometry at 286 nm.

In vitro dissolution profiles of the reference capsules and capsules of the present invention are shown in FIG. 1. The data indicate that the dissolution rate of representative capsules of the present invention are comparable to the reference capsules. Based on U.S. Pat. No. 4,895,726, in vitro dissolution results can be correlated to in vivo absorption in humans. Thus, equivalent or increased dissolution in vitro can result in bioavailability equivalent to the reference in humans.

The invention claimed is:

1. A process for preparing a drug formulation comprising the steps of:
   dissolving a lipid-regulating drug in a solvent free of surfactant to form a drug solution, wherein the drug solution consists of the lipid-regulating drug and the solvent;
   premixing an excipient to generate an admixture;
   wet granulating the admixture and the drug solution to form a granulated drug admixture, wherein the drug solution is not mixed with a second solution prior to wet granulating; and
   drying the granulated admixture.

2. The process of claim 1 wherein the lipid-regulating drug is a fibrate.

3. The process of claim 2 wherein the fibrate is fenofibrate.

4. The process of claim 1 wherein the drying step includes evaporating the solvent.

5. The process of claim 4 wherein the evaporating is performed under vacuum.

6. The process of claim 1 wherein the drying step is accomplished using a fluid bed, tray dryer or rotary atomizer.

7. The process of claim 1 comprising the additional step of adding other excipients.

8. The process of claim 1 comprising the additional step of forming a final dosage form.

9. A process for preparing a drug formulation comprising the steps of:
   dissolving a lipid-regulating drug in a solvent free of surfactant to form a drug solution; wherein the drug solution consists of the lipid-regulating drug and the solvent;
   premixing an excipient to generate an admixture;
   wet granulating the admixture and the drug solution to form a granulated drug admixture; wherein the drug solution is not mixed with a second solution prior to wet granulating;
   drying the granulated admixture; and
   tableting the dried granulated admixture.

10. A process for preparing a drug formulation comprising the steps of:
    dissolving a lipid-regulating drug in a solvent free of surfactant to form a drug solution; wherein the drug solution consists of the lipid-regulating drug and the solvent;
    premixing an excipient to generate an admixture;
    wet granulating the admixture and the drug solution to form a granulated drug admixture; wherein the drug solution is not mixed with a second solution prior to wet granulating;
    drying the granulated admixture; and
    filling capsules with the dried granulated admixture.

11. The process of claim 1 wherein the excipient is one or more members selected from the group consisting of lactose, starch, polyvinyl pyrrolidone, magnesium stearate, and other pharmaceutically-acceptable excipients.

12. The process of claim 1 wherein the admixture is granulated in a fluidized bed.

13. The process of claim 1 wherein the admixture is granulated in a low shear or high shear mixer.

14. A method for treating of hyperlipidemia comprising the step of administering the final drug formulation prepared by the process of claim 9.

15. A method for treating of hyperlipidemia comprising the step of administering the final drug formulation prepared by the process of claim 10.

16. A method for treating of hyperlipidemia comprising the administration of the formulation prepared by the process of claim 3.

* * * * *